US009051577B2

(12) United States Patent
Schuster et al.

(10) Patent No.: US 9,051,577 B2
(45) Date of Patent: Jun. 9, 2015

(54) GLYCO-ENGINEERED ANTIBODIES

(75) Inventors: Manfred Schuster, Schrick (AT); Ralf Kircheis, Vienna (AT); Andreas Nechansky, Oberwaltersdorf (AT); Wolfgang Jost, Freiburg (DE); Gilbert Gorr, Freiburg (DE)

(73) Assignee: GREENOVATION BIOTECH GMBH, Freiburg (DE)

( * ) Notice: Subject to any disclaimer, the term of this patent is extended or adjusted under 35 U.S.C. 154(b) by 1386 days.

(21) Appl. No.: 12/373,268

(22) PCT Filed: Jul. 11, 2007

(86) PCT No.: PCT/EP2007/006123
§ 371 (c)(1),
(2), (4) Date: Jan. 9, 2009

(87) PCT Pub. No.: WO2008/006554
PCT Pub. Date: Jan. 17, 2008

(65) Prior Publication Data
US 2009/0291078 A1 Nov. 26, 2009

(30) Foreign Application Priority Data

Jul. 11, 2006 (EP) .................................... 06450095

(51) Int. Cl.
*C12N 15/82* (2006.01)
*C07K 16/00* (2006.01)
*C07K 16/28* (2006.01)

(52) U.S. Cl.
CPC ............ *C12N 15/8258* (2013.01); *C07K 16/00* (2013.01); *C07K 16/283* (2013.01); *C07K 2317/41* (2013.01); *C07K 2317/732* (2013.01); *C07K 2317/734* (2013.01); *C07K 2317/52* (2013.01)

(58) Field of Classification Search
None
See application file for complete search history.

(56) References Cited

U.S. PATENT DOCUMENTS

| 6,602,684 | B1 | 8/2003 | Umana et al. | 435/69.1 |
| 2004/0077836 | A1* | 4/2004 | DeFrees et al. | 530/351 |
| 2005/0232917 | A1* | 10/2005 | Pullen et al. | 424/141.1 |
| 2006/0029604 | A1* | 2/2006 | Gerngross et al. | 424/143.1 |
| 2006/0034829 | A1 | 2/2006 | Gerngross et al. | 424/133.1 |
| 2006/0182741 | A1* | 8/2006 | Bourel et al. | 424/133.1 |

FOREIGN PATENT DOCUMENTS

| EP | 0 361 902 | 4/1990 |
| EP | 0528767 A1 | 2/1993 |
| JP | 2006-511234 | 4/2006 |
| WO | WO 99/54342 | 10/1999 |
| WO | WO 01/31045 | 5/2001 |
| WO | WO 01/55434 | 8/2001 |
| WO | WO 2004/050838 | 6/2004 |
| WO | WO 2004/057002 | 7/2004 |
| WO | WO 2004/062556 | 7/2004 |
| WO | WO 2005/000225 | 1/2005 |
| WO | WO 2006/005367 | 1/2006 |
| WO | WO 2009/027471 | 3/2009 |

OTHER PUBLICATIONS

Sriraman et al ( Palnt Blotechnol 2:279-87, 2004.*
Lazar et al (Rapid Comm Mass Spec. 18:239-244, 2004.*
Bakker et al (PNAS 98:2899-2904, 2001.*
Bauer et al., "A fast and flexible PEG-mediated transient expression system in plants for high level expression of secreted recombinant proteins," *J. Biotechnol.*, 119:332-342, 2005.
Conrad and Fiedler, "Compartment-specific accumulation of recombinant immunoglobulins in plant cells: an essential tool for antibody production and immunomodulation of physiological functions and pathogen activity," *Plant Mol. Biol.*, 38:101-109, 1998.
Faye et al., "Affinity purification of antibodies specific for Asn-linked glycans containing alpha 1-->3 fucose or beta I-->2 xylose," *Anal. Biochem.*, 209:104-108, 1993.
Fischer et al., "Plant-based production of biopharmaceuticals," *Curr. Opin. Plant Biol.*, 7:152-158, 2004.
Girke et al., "Identification of a novel delta 6-acyl-group desaturase by targeted gene disruption in *Physcomitrella patens*," *Plant J.*, 15:39-48, 1998.
Gomord and Faye, "Posttranslational modification of therapeutic proteins in plants," *Curr. Opin. Plant Biol.*, 7:171-181, 2004.
Gorr and Jost, "Glycosylation design in transgenic moss for better product efficacy," *Bioprocess J.*, 4:26-30, 2005.
Gorr and Wagner, "Humanized glycosylation: production of biopharmaceuticals in a moss bioreacter," *Modern Biopharmaceuticals*, 3: 919-929, 2005.
Hamilton et al., "Characterization of a human ovarian carcinoma cell line (NIH:OVCAR-3) with androgen and estrogen receptors," *Cancer Res.*, 43:5379-5389, 1983.
Harris, "Processing of C-terminal lysine and arginine residues of proteins isolated from mammalian cell culture," *J. of Chromatography A.*, 705:129-134, 1995.
Helenius and Aebi, "Intracellular functions of N-linked glycans," *Science*, 291:2364-2369, 2001.
Hiatt et al., "Production of antibodies in transgenic plants," *Nature*, 342:76-78, 1989.
Hohe and Reski, "Optimisation of a bioreactor culture of the moss *Physcomitrella patens* for mass production of protoplasts," *Plant Sci.*, 163:69-74, 2002.
Huether et al., "Glyco-engineering of moss lacking plant-specific sugar residues," *Plant Biology*, 7:292-299, 2005.

(Continued)

*Primary Examiner* — Lei Yao
(74) *Attorney, Agent, or Firm* — Norton Rose Fulbright US LLP

(57) ABSTRACT

The present invention relates to an antibody preparation comprising modified antibodies of an animal or derivatives or fragments thereof, specific for an antigen, characterized in that • the antibodies or derivatives or fragments thereof comprise an N-glycan structure free of fucose and xylose, and • at least 90%, preferably at least 95%, more preferred at least 99%, most preferred at least 100% of the modified antibodies, derivatives or fragments thereof lack a C-terminal lysine residue.

19 Claims, 6 Drawing Sheets

(56) References Cited

OTHER PUBLICATIONS

Jefferis et al., "IgG-Fc-mediated effector functions: molecular definition of interaction sites for effector ligands and the role of glycosylation," *Immunol. Rev.*, 163:59-76, 1998.

Jost et al., "Isolation and characterisation of three moss-derived beta-tubulin promoters suitable for recombinant expression," *Curr. Genetics*, 47:111-120, 2005.

Kitamura et al., "Establishment and characterization of a unique human cell line that proliferates dependently on GM-CSF, IL-3, or erythropoietin," *J. Cell. Physiol.*, 140:323-334, 1989.

Kolarich and Altmann, "N-Glycan analysis by matrix-assisted laser desorption/ionization mass spectrometry of electrophoretically separated nonmammalian proteins: application to peanut allergen Ara h 1 and olive pollen allergen Ole e I," *Anal. Biochem.*, 285:64-75, 2000.

Koprivova et al., "Targeted knockouts of *Physcomitrella* lacking plant-specific immunogenic N-glycans," *Plant Biotechnol. J.*, 2:517-523, 2004.

Li et al., "Optimization of humanized IgGs in glycoengineered *Pichia pastoris*," *Nat. Biotechnol.*, 24:210-215, 2006.

Lifely et al., "Glycosylation and biological activity of CAMPATH-1H expressed in different cell lines and grown under different culture conditions," *Glycobiology*, 5:813-822, 1995.

Ma et al., "The production of recombinant pharmaceutical proteins in plants," *Nat. Rev. Genet.*, 4: 794-805, 2003.

Mann and Jensen, "Proteomic analysis of post-translational modifications," *Nat. Biotechnol.*, 21: 255-261, 2003.

Niwa et al., "Defucosylated chimeric anti-CC chemokine receptor 4 IgG1 with enhanced antibody-dependent cellular cytotoxicity shows potent therapeutic activity to T-cell leukemia and lymphoma," *Cancer Res.*, 64 (6): 2127-2133, 2004.

Niwa et al., "Enhancement of the antibody-dependent cellular cytotoxicity of low-fucose IgG1 Is independent of FcgammaRIIIa functional polymorphism," *Clin. Cancer Res.*, 10: 6248-6255, 2004.

Preithner et al., "High concentrations of therapeutic IgG1 antibodies are needed to compensuate for inhibition of antibody-dependent cellular cytotoxicity by excess endogenous immunoglobulin G," *Mol. Immunology*, 43:1183-1193, 2003.

Raskin et al., "Plants and human health in the twenty-first century," *Trends Biotechnol.*, 20:522-531, 2002.

Rudd et al., "Glycosylation and the immune system," *Science*, 291:2370-2376, 2001.

Schaefer and Zrÿd, "Efficient gene targeting in the moss *Physcomitrella patens*," *Plant J.*, 11:1195-1206, 1997.

Sharp et al., "Characterization of monoclonal antibody fragments produced by plant cells," *Biotechnol. Bioeng.*, 73:338-346, 2001.

Shields et al., "Lack of fucose on human IgG1 N-linked oligosaccharide improves binding to human Fcgamma RIII and antibody-dependent cellular toxicity," *J. Biol. Chem.*, 277:26733-26740, 2002.

Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.*, 278:3466-3473, 2003.

Sriraman et al., "Recombinant anti-hcg antibodies retained in the endoplasmic reticulum of transformed plants lack core-xylose and core-alpha (1,3)-fucose residues," *Plant Biotechnology Journal*, 2:279-287, 2004.

Trempe, "Human breast cancer in culture," *Recent Results Cancer Res.*, 57:33-41, 1976.

van Ree et al., "Beta(1,2)-xylose and alpha(1,3)-fucose residues have a strong contribution in IgE binding to plant glycoallergens," *J. Biol. Chem.*, 275:11451-11458, 2000.

Weise et al., "Use of *Physcomitrella patens* actin 5′ regions for high transgene expression: importance of 5′ introns," *Appl. Microbiol. Biotechnol.*, 70:337-345, 2006.

Fitchette et al., "Biosynthesis and Immunolocalization of Lewis a-Containing N-Glycans in the Plant Cell," *Plant Physiology*, 121:333-343, 1999.

Bakker et al., "An antibody produced in tobacco expressing a hybrid β-1, 4-galactosyltransferase is essentially devoid of plant carbohydrate epitopes," *Proc. Natl. Acad Sci.*, 103(20): 7577-7582, 2006.

Chen et al., "Modification of Plan N-glycans Processing: The Future of Producing Therapeutic Protein by Transgenic Plants," *Medicinal Research Reviews*, 25(3): 343-360, 2005.

Office Action issued in corresponding European Patent Application No. 07801422.2, dated Feb. 7, 2011.

Cox et al., "Glycan Optimization of a Human Monoclonal Antibody in the Aquatic Plant Lemna Minor," *Nature*, 24(12): 1591-1597, 2006.

Harris, R.J., "Heterogeneity of Recombinany Antibodies: Linking Structure to Function", *State of the Art Analytical Methods for the Characterization of Biological Products and Assessment of Comparability* 122:117-127, 2005.

Office Communication issued in South Korean Patent Application No. 10-2009-7002684, issued Dec. 10, 2013.

Harris R J: "Processing of C-terminal lysine and arginine residues of proteins isolated from mammalian cell culture" Journal of Chromatography A, Elsevier, Amsterdam, NL, vol. 705, No. 1, Jun. 23, 1995, pp. 129-134.

Harris R J et al: "Structural Characterization of a Recombinant CD4-IGG Hybrid Molecule", European Journal of Biochemistry, Blackwell Publishing, Berlin, DE, vol. 194, No. 2, Jan. 1, 1990, pp. 611-620.

Sriraman Rajan et al: "Recombinant Anti-HCG Antibodies Retained in the Endoplasmic Reticulum of Transformed Plants Lack Core-Xylose and Core-Alpha(1,3)-Fucose Residues" Plant Biotechnology Journal, Blackwell, Oxford, GB, vol. 2, No. 4, Jul. 2004, pp. 279-287.

Santora L C et al: "Characterization of recombinant human monoclonal tissue necrosis factor-alpha antibody using cation-exchange HPLC and capillary isoelectric focusing", Analytical Biochemistry, Academic Press Inc, New York, vol. 275, No. 1, Nov. 1, 1999, pp. 98-108.

Lewis Derf A et al: "Characterization of humanized anti-TAC, an antibody directed against interleukin 2 receptor, using electrospray ionization mass spectrometry by direct infusion, electrospray ionization mass spectrometry by direct infusion, LC/MS, and MS/MS", Analytical Chemistry, American Chemical Society, US, vol. 66, No. 5, Jan. 1, 1994, pp. 585-595.

Radaev S et al: "Recognition of IgG by Fcgamma receptor. The role of Fc glycosylation and the binding of peptide inhibitors", Journal of Biological Chemistry, American Society for Biochemistry and Molecular Biology, Inc, US, vol. 276, No. 19, May 11, 2001, pp. 16478-16483.

EPO Communication issued in European Patent Application No. 11163178.4, dated Sep. 3, 2012.

Office Action dated Feb. 26, 2015 for corresponding Korean Application No. 10-2009-7002684 (Machine translation included).

\* cited by examiner

Fig. 1:

DIVMTQSPLS LPVTPGEPAS ISCRSSQSIV HSNGNTYLEW
YLQKPGQSPQ LLISKVSNRF SGVPDRFSGS GSGTDFTLKI
SRVEAEDVGV YYCFQGSHVP FTFGQGTKLEIK

Fig. 2:

Seq.1:
EVQLLESGGG LVQPGGSLRL SCAASGFTFS DYYMYWVRQA
PEKRLEWVAY ISNGGGSSHY VDSVKGRFTI SRDNSKNTLY
LQMNSLRAED TALYHCARGM DYGAWFAYWG QGTLVTVSS

Seq. 2:
EVQLLESGGG LVQPGGSLRL SCAASGFTFS DYYMYWVRQA
PEKRLEWVAY ISNGGGSSHY VDSVKGRFTI SRDNAKNTLY
LQMNSLRAED TALYHCARGM DYGAWFAYWG QGTLVTVSS

| IGN311 | IGN314 |
|---|---|
| GlcNAc$_2$Man$_3$GlcNAc$_2$Fuc | GlcNAc$_2$Man$_3$ |
| GlcNAc$_2$Man$_3$GlcNAcFuc | GlcNAc$_2$Man$_3$GlcNAc |
| GlcNAc$_2$Man$_3$GlcNAc$_2$FucGal | GlcNAc$_2$Man$_3$GlcNAc$_2$ |
| GlcNAc$_2$Man$_3$GlcNAc$_2$FucGal$_2$ | |

GLYCO-ENGINEERED ANTIBODIES

This application is a national phase application under 35 U.S.C. §371 of International Application No. PCT/EP2007/006123 filed 11 Jul. 2007, which claims priority to European Application No. 06450095.2 filed 11 Jul. 2006. The entire text of each of the above-referenced disclosures is specifically incorporated herein by reference without disclaimer.

The invention relates to the field of modified antibodies, derivatives or fragments thereof.

The pharmaceutical industry increasingly encounters the need for cost effective alternative large scale production systems of biopharmaceuticals. Plant-based expression systems have meanwhile demonstrated their usefulness as a suitable alternative to animal cell factories. Especially, their low production costs combined with exceptional safety through minimized risks of contamination due to the absence of human pathogens (Raskin, I. et al., Trends Biotechnol 20, 522-531 (2002); Fischer, R. et al., Curr Opin Plant Biol 7, 152-158 (2004)) is of utmost importance. Plants are able to perform most of the higher eukaryotic posttranslational modifications (Gomord, V. & Faye, L., Curr Opin Plant Biol 7, 171-181 (2004)). These include complex glycosylations, protein processing and folding as well as the assembly of complex multimeric proteins, features that contribute to the bioactivity and the pharmacokinetics of active therapeutic antibodies. Hence, various recombinant proteins, including human antibodies, have been expressed successfully in plant host expression systems (Hiatt, A. et al., Nature 342, 76-78 (1989); Ma, J. K. et al., Nat Rev Genet 4, 794-805 (2003)).

Nevertheless plant derived N-linked oligosaccharides differ considerably from those found in humans. Besides the general absence of α1,6-fucosyl residues in plants, differences in posttranslational modifications, such as glycosylation, have been shown to influence the properties of plant-derived proteins (Daniell et al., supra; Conrad et al. (1998) Plant Mol. Biol. 38:101-109; Mann et al. (2003) Nat. Biotechnol. 21:255-261). In plants, N-linked glycans may contain antigenic (Faye et al. (1993) Anal. Biochem. 109:104-108) and/or allergenic (van Ree et al. (2000) J. Biol. Chem. 275:11451-11458) β(1,2)-xylose (Xyl) residues attached to the N-linked Mannose of the glycan core and α(1,3)-fucose (Fuc) residues linked to the proximal GlcNAc that are not present on mammalian glycans. In contrast sialic acid residues are normally not attached to plant N-glycans. However, plant antibodies do not require these residues for successful topical passive immunization (Ma et al., supra).

Glycosylation processing in the endoplasmic reticulum (ER) is conserved amongst almost all species and restricted to oligomannose ($Man_{5-9}GlcNAc_2$) type N-glycans, whereas the Golgi-generated processing to hybrid and complex type glycans is highly diverse (Helenius et al. (2001) Science 291:2364-2369). ER retention of expressed proteins in transgenic plants usually improves the production levels (Conrad et al. (1998) Plant Mol. Biol. 38: 101-109; Sharp et al. (2001) Biotechnol. Bioeng. 73:338-346). However, since glycan processing can affect the stability of antibodies (Rudd et al. (2001) Science 291:2370-2376), it is unclear whether an antibody derived from plant expression systems with modified glycan structures would be active and able to confer effective systemic post-exposure prophylaxis.

As large-scale compatible production platform for recombinant proteins in contained suspension cultures the robust moss *Physcomitrella patens* offers an absolute animal free, component free, next generation production technology by combining several beneficial attributes with an—not only among land plants—extraordinarily high rate of homologous nuclear DNA recombination allowing an efficient targeted knockout of genes (Gorr, G. & Wagner, S., Modern Biopharmaceuticals 3, 919-929 (2005); Girke, T. et al., Plant J 15, 39-48 (1998); Schaefer, D. G. & Zyrd, J. P; Plant J 11, 1195-1206 (1997). In attempts to "humanize" N-linked oligosaccharide structures, double knockout variants for β1,2-xylosyltransferase and α1,3-fucosyltransferase genes (Δxyl-t/Δfuc-t) have recently been generated according to WO 04/057002. These moss variants synthesized total glycoproteins completely lacking the two plant-specific sugar residues yet they were not affected in morphology, growth, development and the ability to secrete recombinant glyco-proteins (Koprivova, A. et al.; Plant Biotechnol J 2, 517-523 (2004); Huether, C. M. et al. Plant Biol 7, 292-299 (2005)). The successful attachment of terminal, human-like 1,4 linked galactose to N-glycans from moss has been shown also (Huether, C. M. et al. Plant Biol 7, 292-299 (2005); Gorr and Jost Bioprocess J 4, 26-30 (2005)). Functional characteristics of the antibodies like ADCC (antibody-dependent cell-mediated cytotoxicity) and CDC (complement-dependent cytotoxicity) activity were not disclosed there.

Although there have been attempts to produce antibodies by plant expression systems, stability of the antibodies due to changed glycosylation patterns and negative effects on effector function and interaction between Fc regions and Fc receptors of these antibodies have been described. Functions mediated by the Fc-part of immunoglobulins, have been reported to be strongly related to their N-linked oligosaccharide structures (Jefferis, R. et al., Immunol Rev 163, 59-76 (1998)).

Particularly core fucosylated oligosaccharides showed weaker binding to the FcγRIIIa receptor (CD16) expressed on effector cells and resulted in a decreased lytic potential (Shields, R. L. et al., J Biol Chem 277, 26733-26740 (2002); Shinkawa, T. et al., J Biol Chem 278, 3466-3473 (2003)). In contrast, yeast produced antibodies lacking core fucose in its N-glycan pattern showed weak potential in a B-cell depletion assay. Only high concentrations of the antibody resulted in a depletion of B-cells from a healthy donor. Characteristics of the antibodies like ADCC and CDC activity were not disclosed there.

However, following the production of the antibody in vivo most of the N-glycan structures presented in this study were processed in vitro in further steps by the use of specific enzymes to achieve the final N-glycan patterns (Li et al., Nat Biotechnol, doi: 10.1038/nbt1178 (2006).

The U.S. Pat. No. 6,602,684 describes methods to increase the effector function of an antibody by modifying complex glycan structures, such as bisected N-linked glycan structures modified by GnTIII.

Monoclonal antibodies against rabies are described in the WO 2005/000225 A2. These antibodies are of the IgG, IgA, IgM, IgD and IgE class, are produced in plants lack N-glycan structures with alpha-1,3-fucose residues and have less allergenic plant epitopes.

The WO 2004/050838 A2 describes immunoglobins against herpes simplex virus produced in plants without fucose residues but may comprise xylose.

The disclosure of the WO 01/31045 A1 relates to a method of producing proteins with mammal-like glycostructure in plants. Preferably the plants do not have an active fucosyltransferase or xylosyltransferase.

The US 2006/0034829 A1 describes immunoglobins with a N-glycan structure of the formula $Man_3GlcNAc_2$.

The US 2006/0029604 A1 describes immunoglobins with a N-glycan structure of the formula $GlcNac_2Man_3GlcNac_2$. These structures are generated by β-galactosidase treatment.

The WO 01/55434 A1 relates to the inhibition of carbohydrate modifying enzymes in plants, in particular GBSS and GnTI.

Even in view of the long and intensive research on development of antibodies, there is still a high demand for antibodies with improved characteristics like increased effector functions.

The object of the invention is to provide antibodies with improved properties.

According to the invention, this object is achieved by the subject matter of the claims.

The present invention provides an antibody preparation comprising modified antibodies of an animal, preferably a mammal, or derivatives or fragments thereof, specific for an antigen, characterized in that the antibodies or derivatives or fragments thereof comprise an N-glycan structure free of fucose and xylose, and the ADCC activity of the preparation is by at least 10% less inhibited in an at least 10% serum solution (100% being undiluted serum) which comprises unspecific antibodies of the animal than an unmodified antibody preparation of the animal specific for the same antigen, and/or at least 90%, preferably at least 95%, more preferred at least 99%, most preferred at least 100% of the modified antibodies, derivatives or fragments thereof lack a C-terminal lysine residue.

It was found that the effector function of therapeutical antibodies is generally inhibited by the normal antibody background normally found in body fluids. In natural serum high concentrations of therapeutic IgG (e.g. human IgG1 or IgG3, or murine IgG2a) antibodies are needed to compensate for inhibition of antibody-dependent cellular cytotoxicity (ADCC) by excess endogenous immunoglobulin G. Human serum has an average antibody concentration of approximately 11.7 mg/ml, wherein IgG1 and IgG3 constitute the majority (together 7.7 mg/ml). Normal serum IgG levels are blocking the binding of a therapeutic IgG antibody to the low affinity IgG receptor (FcγRIIIa, CD16) which is present on NK cells. Together with CD64, these two Fcγ receptors are the main cellular receptors mediating ADCC. ADCC lysis can be increased through different glycosylation structures (e.g. WO2006/005367). However these antibodies could still be inhibited by unspecific serum antibodies (Preitner et al., Mol. Immmol. 43, 1183-1193 (2003)). It was now surprisingly found that a preparation of antibodies having a N-glycan structure free of fucose and xylose, in particular lacking the C-terminal lysine, preferably also free of galactose, is increasingly resistant to this inhibition at a significant degree.

The reference to the unmodified antibody preparation of the animal, in particular a mammal, specific for the same antigen is to be understood that with the antibody according to the present invention the effector function on the C-terminal portion of the antibody is modified. Of course the lytic activity (ADCC) is also dependent on the affinity of the antibody to its target from which the lytic effector function mediated by the Fc portion should be considered to be independent. The unmodified antibody normally comprises an N-glycan structure with galactose, fucose (especially α1,3-fucose) and/or xylose (especially β1,2-xylose). Preferably both the inventive modified antibody and the unmodified (i.e. parental) antibody are monoclonal antibodies and more preferred recombinantly expressed (or designed for recombinant expression) in cell expression system e.g. plant cells.

Alternatively to a comparative serum solution (which can e.g. be diluted to approximately 10% serum) an antibody composition of unspecific antibodies can be used. Such a comparative antibody composition can have physiological antibodies of an animal or it can be a parental (unmodified) antibody preparation of the inventive (modified) antibody. The comparative antibodies can be in concentrations similar to serum antibodies, e.g. 0.5 mg/ml to 15 mg/ml, preferably 1 mg/ml to 5 mg/ml, more preferred 3 mg/ml. Preferably the comparative antibodies are IgG1 and IgG3. Given the approximate serum IgG1 and IgG3 levels in serum of 7.7 mg/ml 10% serum would amount to 0.77 mG/ml and 40% serum to 3.08 mg/ml IgG1 and IgG3.

Novel antibodies which have this resistance, as well as derivatives, fragments or a preparation thereof can be produced in recombinant cells, preferably plant cells, being deficient in β1,2-xylosyltransferase and α1,3-fucosyltransferase.

Preferably the N-glycan structures of the antibodies or derivatives or fragments thereof are also free of galactose. The lack of galactose can be achieved by expression in adequate expression system, like specific plant cell expression system, or by treatment with galactosidase or by expression in cells, e.g. animal cells, which lack 1,4 galactosyltransferase activity.

Preferably the unmodified antibody preparation has the same affinity to the antigen as the preparation of the modified antibodies or derivatives or fragments thereof.

In the preparation preferably at least 90%, preferably at least 95%, more preferred at least 99%, most preferred 100% of the modified antibodies, derivatives or fragments thereof lack a C-terminal lysine residue, in particular determined on the sum of the heavy chains (which normally can comprise lysine). Since antibodies can have more chains which potentially comprise the C-terminal lysine it is understood that the quantitative percentage of the lack of lysine refers to all chains which potentially have the C-terminal lysine. It was shown that monoclonal antibodies are heterogenous in the presence of the C-terminal lysine (Lazar et al., Rapid Communications in Mass Spectrometry (18), 3, 239-244, 2004). It was surprisingly found that antibodies with quantitatively removed (or not expressed) C-terminal lysine have significant advantageous effector functions over other antibodies. It was shown herein that the ADCC can be inhibited in serum dilutions by the physiological present antibodies. This inhibitory effect was not present (or significantly reduced) in the inventive antibodies of this embodiment lacking the C-terminal lysine.

Furthermore the N-glycan structure of the antibodies or derivatives or fragments thereof is preferably selected from $GlcNAc_2Man_3$, $GlcNAc_2Man_3GlcNAc$ or $GlcNAc_2Man_3GlcNAc_2$. Preferably the $GlcNAc_2Man_3GlcNAc_2$ structure is comprised by at least 50% of the antibodies, fragments or derivatives thereof, more preferred by at least 70% or most preferred by at least 90%. In other embodiments the preferred structures are $GlcNAc_2Man_3$ and/or $GlcNAc_2-Man_3GlcNAc$, in particular wherein the $GlcNAc_2Man_3$ and $GlcNAc_2Man_3GlcNAc$ structures are present in at least 30%, preferably at least 50%, more preferred at least 70% of the N-glycan structures of the modified antibodies or derivatives or fragments thereof.

In special embodiments of the preparation of the antibody less than 50%, preferably less than 30%, more preferred less than 10% of the antibodies, derivatives or fragments thereof lack the N-glycan structure. The N-glycan structure, which is bound to $Asn_{297}$ in human IgG antibodies is preferably present in most antibodies of the preparation.

The animal from which the modified antibodies (as well as its fragments and derivatives) derive is preferably a mammal, in particular embodiments a human or a mouse, or a reptile, in particular embodiments a crocodile, —although the antibodies can be expressed recombinantly in other organisms such as plant cells.

Preferably the ADCC activity of the preparation is by at least 10% less inhibited, especially preferred by at least 15%, 20%, 25% or even 30% less inhibited, in an at least 10%, preferably at least 40%, serum solution comprising unspecific antibodies of the animal than an unmodified antibody preparation of the animal specific for the same antigen. The novel antibodies have this exceptional resistance to masking effects of other antibodies found in body fluids (e.g. serum) of the animal. Preferably the ADCC activity of the preparation is by at least 20%, preferably at least 30%, less inhibited in the solution of unspecific antibodies.

Among the preferred forms of the antibodies are chimeric, humanized or human antibodies, preferably IgG antibodies.

In a special embodiment of the invention a preferred feature of the antibody preparation is that the CDC activity is at least 10% decreased as compared to an unmodified antibody preparation specific for the same antigen. In another embodiment the preparation has an at least 10 fold increased ADCC activity in comparison to an unmodified antibody preparation of the animal specific for the same antigen.

In preferred embodiments binding of the modified antibodies, derivatives or fragments thereof to $CD16_{158\ F/F}$ is by at least 10% less inhibited in an at least 10%, preferably at least 40%, serum solution comprising unspecific antibodies of the animal than an unmodified antibody preparation of the animal specific for the same antigen.

Preferably cell lysis of targets of the modified antibodies, derivatives or fragments thereof mediated by effector cells of either $CD16_{158}$ genotype is by at least 10% less inhibited in an at least 10%, preferably at least 40%, serum solution comprising unspecific antibodies of the animal than an unmodified antibody preparation of the animal specific for the same antigen.

In another aspect the present invention provides an antibody preparation obtainable through expression of a nucleic acid(s) encoding an antibody, a fragment or derivative thereof in cells, preferably plant cells, being deficient in β1,2-xylosyltransferase and α1,3-fucosyltransferase activities. Such an antibody preparation is preferably further characterized by the above described functional and structural advantages. It is understood that an antibody, a fragment or a derivative thereof can be comprised by more than one amino acid chain and more than one nucleic acid (e.g. one for each chain) may be necessary for the expression. Of course more than one chain can be encoded by one nucleic acid, e.g. on one vector.

Preferably the antibody preparation is obtainable in the cells are also deficient in galactosyltransferase, preferably the cells completely lack galactose-1-phosphate-uridyl-transferase or any galactosyltransferase.

In special embodiments the antibody preparation is obtainable in expression systems which are enabled to attach galactose residues in 1,4 linkage to the terminal GlcNAc residues of N-glycans. Such expression systems may comprise natural galactosyltransferase activity or may be genetically engineered to achieve the specific galactosyltransferase activity.

Preferably the antibody preparation is expressed in cells with GnTIII activity, especially as disclosed in the U.S. Pat. No. 6,602,684 or the WO99/54342. The GnTIII activity leads to further improved lytic effector functions (e.g. introduction of bisecting structures). The cells are for example transfected with a GnTIII gene which results in increased GnTIII expression compared to untransfected or unmodified cells.

The present invention provides in another aspect a modified antibody or derivative or fragment thereof, characterized in that the glycan structure of said antibody is free of fucose and xylose, preferably also free of galactose, and the N-glycan structure is either $GlcNAc_2Man_3$, or $GlcNAc_2Man_3GlcNAc$ or $GlcNAc_2-Man_3GlcNAc_2$. The N-glycan structure follows preferably the formula -β-1,4-GlcNAc-β-1,4-GlcNAc-(β-1,4-Man)(α-1,6-Man)(α-1,3-Man), wherein one (or both) of the α-mannose residues may bind an additional β-1,4-GlcNAc (FIG. 4). The core glycosylation is generally found on Asn297 in IgG antibodies.

In a particular aspect the present invention relates to a monoclonal antibody or derivative or fragment thereof that recognizes the Lewis Y antigen and is derived from a parental (i.e. the unmodified antibody) monoclonal antibody recognizing the Lewis Y antigen and comprising galactose, fucose or xylose wherein the glycan structure of said monoclonal antibody is free of fucose and xylose, preferably also free of galactose, the ADCC effector function is at least 10-fold increased and antigen binding specificity and affinity of said antibody is identical or similar to the unmodified parental antibody. For this embodiment any antibody recognizing Lewis-Y can be used as parental antibody.

A preferred parental monoclonal antibody is an antibody comprising a humanized light chain variable region, a human light chain constant region, a humanized heavy chain variable region and a human heavy chain constant region, wherein the humanized light chain variable region can have at least parts of the amino acid sequence as shown in FIG. 1 and the humanized heavy chain variable region can have at least parts of the amino acid sequence as shown in FIG. 2. Preferably, the amino acid sequence of the inventive antibody is identical to the parental antibody. For example, the antibody derivative can be a chimeric one according to EP 0 528 767. In special embodiments the antibody derivative is a single chain antibody (SCA). SCAs are for example disclosed in the U.S. Pat. No. 4,946,778. In comparison to the unmodified parent antibody which is encoded by the same DNA but expressed in a animal, e.g. mammalian, host, the antibody according to the invention can exhibit identical or similar assembly, folding, specificity and bivalence and preferably does not show a higher degree of degradation or aggregation.

The antibody derivative can be selected from the group of recombinant or artificial, including single chain antibodies, antibodies, in particular humanized antibodies from an animal. In particular antibodies from camels or reptiles like crocodiles are preferred which are minimally antigenic in humans. The antibody fragments may comprise or be selected from constant and/or variable portions of an antibody in particular selected from Fc, Fc-like, Fv, Fab, F(ab)$_2$, Fab', F(ab')$_2$, scFv, scfc, $V_{HH}$. Most preferred the antibody fragment is an Fc-like or Fc fragment with the inventive glycosylation structure.

The clinical efficacy of the parental antibody is related to the biological activity of the Fc part of the human IgG1 molecule, which is determined by its efficiency in inducing antibody dependent cellular cytotoxicity (ADCC). The ADCC function depends on the glycosylation of the Fc part, which interacts with the FcγRIII on granulocytes and monocytes (Lifely et al., 1995, Glycobiology, 5(8), 813-822).

The ADCC effector function of the antibody and/or the preparation according to the invention is at least 5 fold increased, preferably at least 10 fold, more preferably at least 20 fold or even at least 30 fold increased, even more preferred at least 40 fold increased, most preferred at least 50 fold increased compared to the ADCC activity of the parental antibody, i.e. compared to the unmodified antibody preparation specific for the same antigen. The ADCC effector function is best determined by cell lysis of cells expressing the antigen against which the antibody is directed (EC50-value of the lysis). As an antigen compound against which antibodies can generally be directed is understood (e.g. any protein, glycoprotein, nucleic acid, etc.). The antigen may have one epitope or alternatively more than one epitope. Preferably the antibodies are directed against the same epitope as in monoclonal antibodies.

The ADCC lysis activity of the inventive antibody can be measured in comparison to the parental antibody using cells with target antigens in cell lysis assays. In cases of antibodies directed against the Lewis-Y antigen Lewis-Y positive target cancer cell lines, for example SKBR5, SKBR3, LoVo, MCF7, OVCAR3 and Kato III can be used as targets.

Effector cell mediated tumor cell lysis can strongly depend on the interaction between immunoglobulin Fc domains and Fc receptors on effector cells. CD16 receptor expressed on NK cells has been reported to bind, depending on its phenotype, with different affinities to IgG (Niwa et al., Cancer Res 64, 2127-2133). The CD16 genotype of PBMC donors was therefore analysed and it was found that only about 50% (5 out of 10) expressed the high affinity phenotype ($CD16_{158V/V}$). ADCC assays performed with such PBMC donors showed a strongly enhanced lytic activity with parental antibody preparations and the antibody according to the invention, when compared to NK cells expressing the low affinity receptor ($CD16_{158F/F}$). The side by side comparison on Ovcar-3 cells revealed an enhancement of the lytic potential for the antibody according to the invention of a factor of approx. 40, independently from the chosen CD16 phenotype.

The antibody according to the invention can be a murine, chimeric, human or humanized antibody, preferably the antibody is a humanized one. In a preferred embodiment, the antibody is IgG or a fragment or derivative thereof, preferably IgG1 or a fragment or derivative thereof. In a further embodiment, the present inventive antibody is a fusion protein that includes a region equivalent to the Fc region of human IgG.

Accordingly, in one aspect the invention is also directed to a pharmaceutical preparation containing the antibody according to the invention in a pharmaceutically acceptable carrier or diluent.

Furthermore, the present invention relates to the use of this antibody as a pharmaceutical.

The pharmaceutical can be used as medicament for the prophylactic and/or therapeutic treatment for the reduction or inhibition, respectively, of the growth of tumor cells in a patient, especially for the treatment of solid cancer, exemplary for the treatment of metastasized tumors or disseminated tumor cells of epithelial origin. Furthermore, the antibody according to the invention can be used for the treatment of minimal residual disease.

The antibody according to the invention at a given concentration was able to lyse target cells with a broader range of antigen densities. This phenomenon may be of relevance in tumor therapy especially since target antigen densities can not be considered as constant on epithelial tumors and may vary both in the primary tumors and on derived metastasis. In summary, active therapeutic antibodies expressed by glyco-optimized production strains—such as the moss-produced antibody IGN314—do show an enhanced lytic activity and may reduce therapeutic doses or, at a given concentration, lyse a broader spectrum of tumor cells with different antigen densities. Especially cells with low antigen densities, which would escape to standard therapeutic antibodies but, may be targeted and destroyed by such glyco-engineered antibodies. On top of this, glyco-optimized antibodies showed lower EC50 values on all investigated cell lines and on both $CD16_{158}$ phenotypes which is indicative of a higher affinity to both $CD16_{158F/F}$, $CD16_{158V/V}$ phenotypes. This stronger interaction reduces EC50 concentrations and enables a reduction of the threshold concentration necessary to initiate target cell lysis for both phenotypes. This phenomenon can bring a therapeutic benefit especially for patients carrying the low affinity phenotype, which would otherwise require higher antibody concentrations for the same therapeutic effect when treated with classical antibody preparations.

In a further aspect of the present invention a method for the manufacture of an antibody or antibody mixture is provided, wherein the antibody is expressed in cells, preferably plant cells, being deficient in β1,2-xylosyltransferase and α1,3-fucosyltransferase activity, preferably completely lacking β1,2-xylosyltransferase and α1,3-fucosyltransferase activities, as well as the antibody obtainable by this expression. E.g. at least one vector comprising nucleic acids encoding antibody chains can be used to transform a cell or plant cell which in turn can be multiplied and used to produce the modified antibody.

Preferably the cells are also deficient in 1,4 galactosyltransferase activity.

In preferred embodiments the DNA encoding the antibodies, fragments or derivatives used to express the antibodies, fragments or derivatives lacks the codon for the C-terminal lysin.

In other embodiments the C-terminal lysin of the antibodies, fragments or derivatives is removed, preferably by a carboxy peptidase, e.g. carboxypeptidase B, or in vivo by the selection of appropriate cell culture conditions, preferably by selection of animal cell expression systems. Expression is preferably in BY2 cells, carrot cells, yeast (e.g. *pichia* or *saccharomyces*), ciliates, algae or insect cells.

BRIEF DESCRIPTION OF THE FIGURES

FIG. 1: Sequences of the humanized light chain variable region of the Lewis Y targeting monoclonal antibody IGN314 (SEQ ID NO: 1).

FIG. 2: Sequence of the humanized heavy chain variable region of the Lewis Y targeting monoclonal antibody IGN314. Either sequence 1 (SEQ ID NO: 2) or 2 (SEQ ID NO: 3) can be used.

(a) Silver-stained SDS-polyacrylamide gels of purified IGN314 in comparison to the parent antibody IGN311. IGN311 is a humanized monoclonal IgG anti-Lewis Y antibody. Under non-reducing conditions (left panel), both samples showed exactly the same protein bands in the range of approximately 150 kDa corresponding to the expected molecular weight of intact, correctly assembled IgG. (−) Simultaneously purified culture supernatant of mock-transformations. Under reducing conditions (right panel), solely protein bands of approximately 50 and 25 kDa could be detected, corresponding to IgG heavy and light chains, respectively.

(b) Size exclusion HPLC analysis of IGN314. The expression product eluted as a sharp peak at a retention time of 8.6 min characteristic for intact IgG. Less abundant (less than 10%), not fully resolved peaks of shorter retention times of 7.4 and 7.9 min appeared, which may probably correspond to a minor amount of aggregated antibody structures like IgG multimers. (c) Verification of IGN314 specificity by testing its activity to bind antigen in an anti-idiotypic sandwich ELISA (Runs test). Dilution curves are displayed graphically in comparison to IGN311. Curves were fitted using a sigmoid four parameter fit (goodness of fit: $R^2 > 0.99$).

Figures 4, 5:
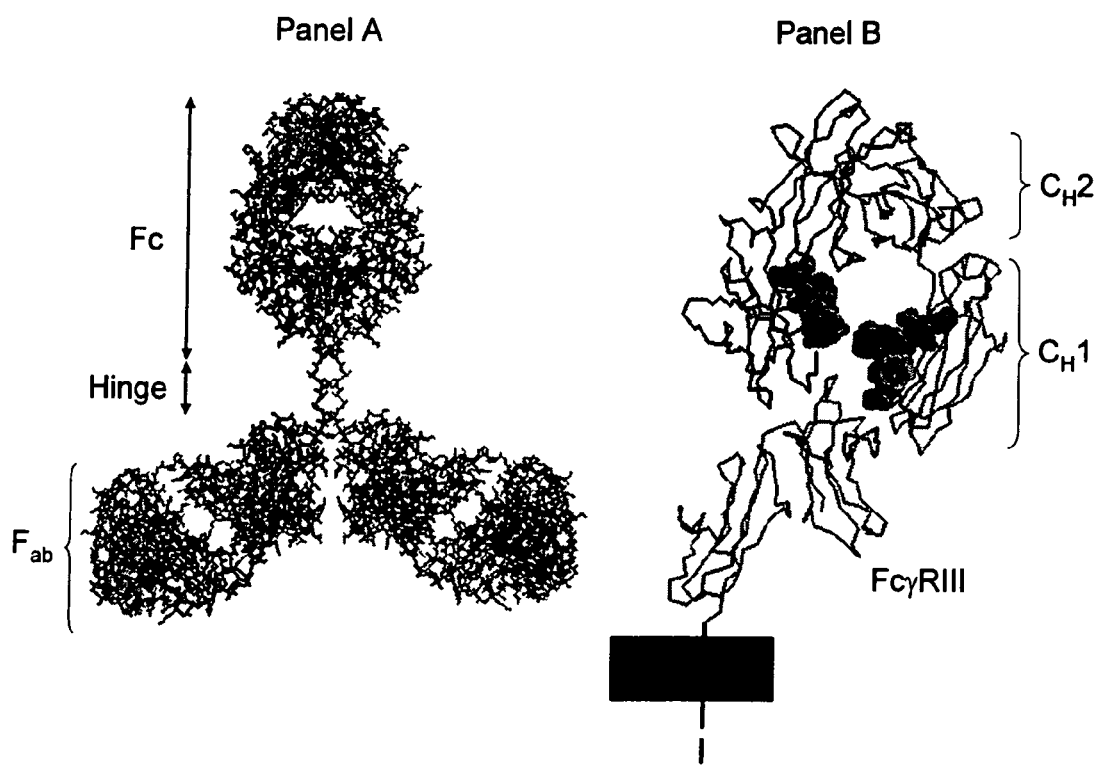

FIG. 4: N-Glycosylation of IGN311 and IGN314

A Table of glycan structures deduced from the respective mass spectra is given. Tryptic digested peptides obtained from SDS-polyacrylamide gel bands of the heavy chains of antibodies IGN311 (parental) and IGN314 (glyco-modified) were separated by HPLC and analyzed by electrospray ionization mass spectrometry. The glycan masses were calculated relating to the detected masses of the glycopeptides of the sequence TKPREEQYN$^{297}$STYR (SEQ ID NO: 4) (with one unused tryptic cleavage site) or EEQYN$^{297}$STYR (SEQ ID NO: 5). Glycan structures are deduced from the respective mass increment. GlcNAc=N-acetylglucosamine, Man=mannose, Fuc=1,6 linked fucose, and Gal=1,4 linked galactose residues. GlcNAc residue may be attached to either of the two antennae. Gal residue may be attached to either of the two antennae. Fuc residue is attached to the proximal GlcNAc residue.

FIG. 5: Structure of human IgG1-Fc and interaction with FcγRIII (CD16). Panel A: General structure of an IgG antibody. The murine IgG2a antibody was crystallized by Harris et al 20 (Brookhaven Protein Databank code 1IGT). The two heavy chains are show in dark and light blue, respectively. The two light chains are shown in green and yellow, respectively. In red, the carbohydrate moieties attached to Asn297 of the heavy chains are indicated. Panel B: Interaction of human IgG1-Fc with FcγRIII (CD16). The complex was crystallized and published in Brookhaven Protein Databank code: 1T89). A ribbon model of human Fc (consisting of CH1 and CH2) is shown with the two heavy chain components in light blue and violet, respectively. The extracellular region of CD16, attached to the cell surface (grey box), is shown in green. The broken line indicates that CD16 either exists as signaling competent molecule or as GPI-linked (non-signaling competent) molecule. The location of the fucose residue which is not present in the glyco-engineered IGN311 variant is encircled (orange).

Figure 6:
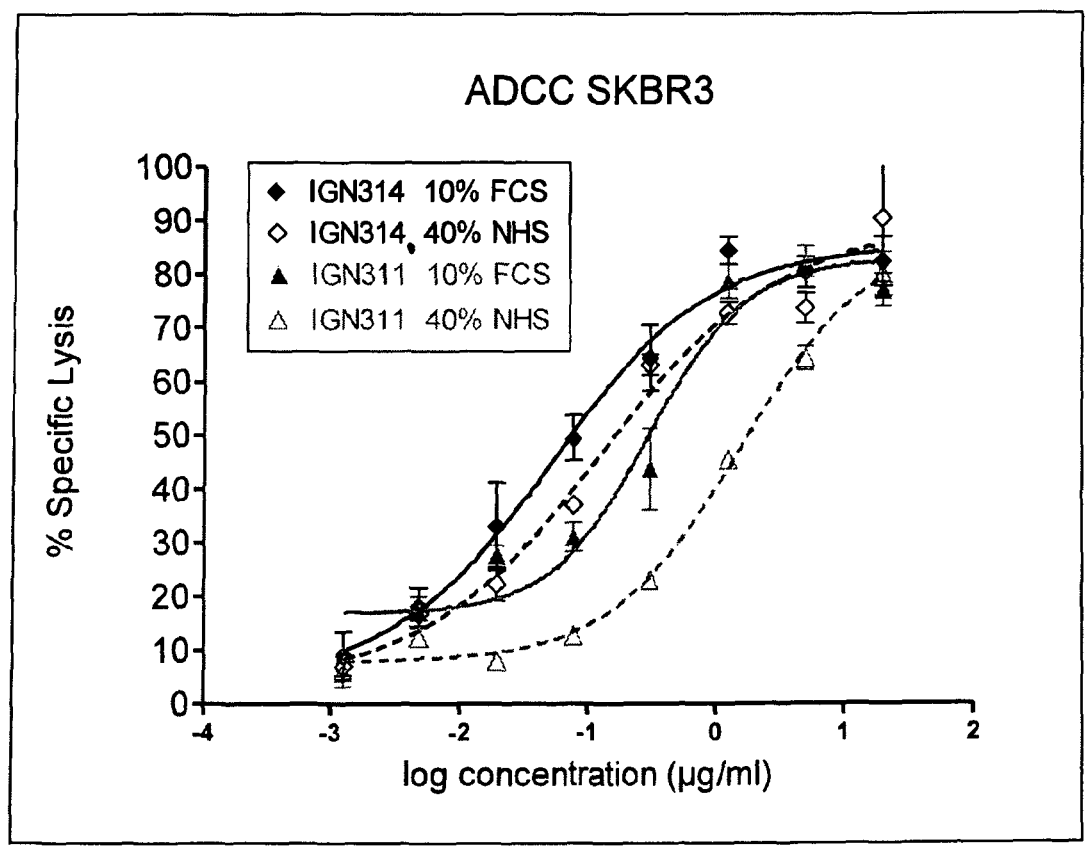

FIG. 6: Comparison of ADCC mediated lysis of tumor cells by human PBMC mediated by parental antibody IGN311 (grey line) and moss-derived de-fucosylated variant IGN314 (black line): Effect of human serum on antibody mediated cell lysis (ADCC) in different serum matrixes. Samples were diluted with RPMI 1640 in constant matrix (10% FCS or 40% NHS, respectively) and ADCC mediated lysis of SK-BR-3 tumor cells by human PBMC was measured in triplicates. Data were fitted using a four-parameter sigmoid fit (goodness of fit, $R^2$>0.92 for all cases). The lysis potential was evaluated at $EC_{50}$: 0.301 µg/ml (95% CI: 0.169-0.537) and 0.052 µg/ml (95% CI: 0.028-0.094) for the parental IGN311 wild-type and the glyco-modified IGN314, respectively, in 10% FCS and 1.558 µg/ml (95% CI: 0.989-2.457) and 0.126 µg/ml (95% CI: 0.065-0.244) for parental IGN311 and glyco-modified IGN314, respectively, in 40% NHS.

Figure 7A:
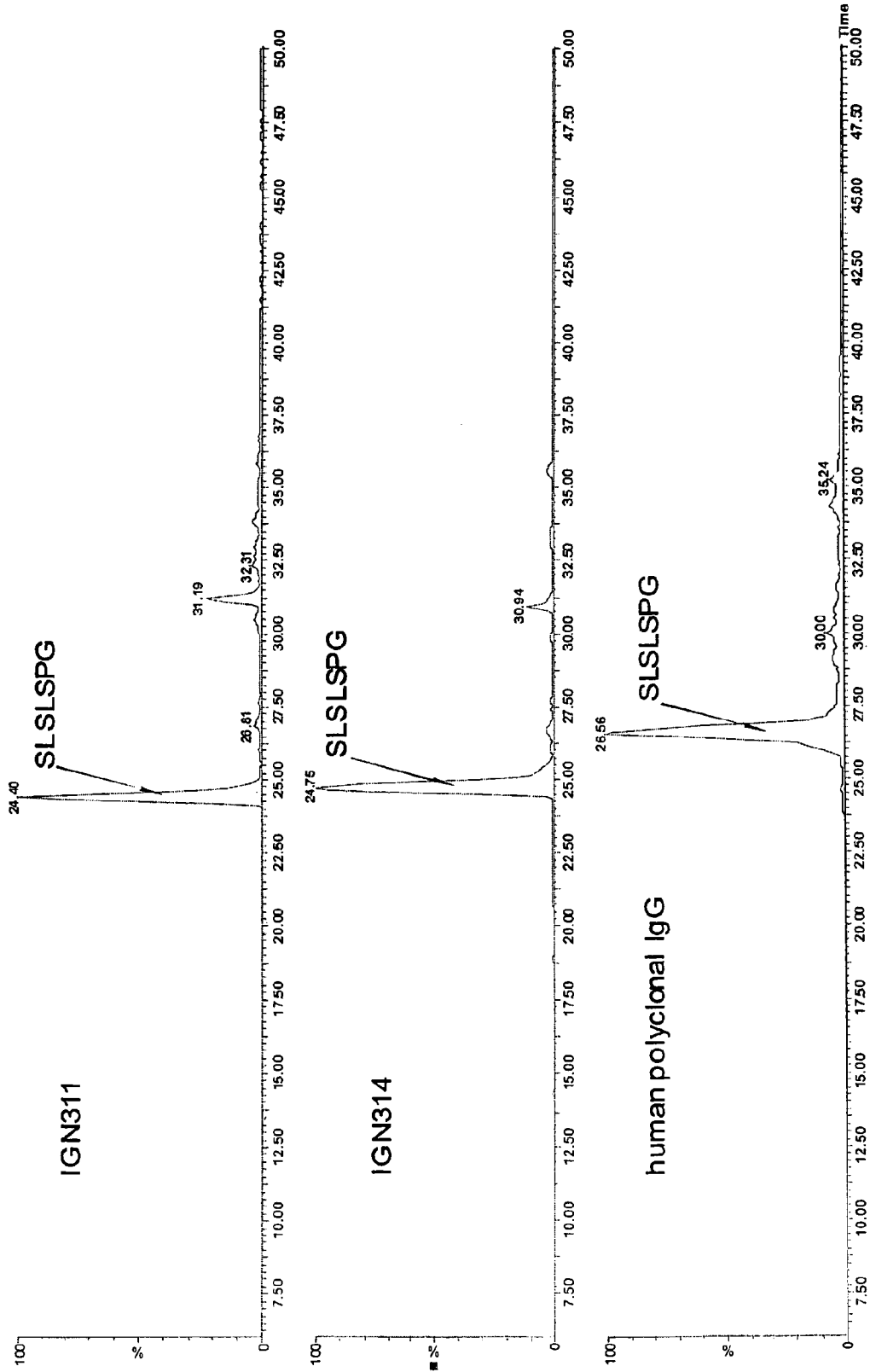
Figure 7B:
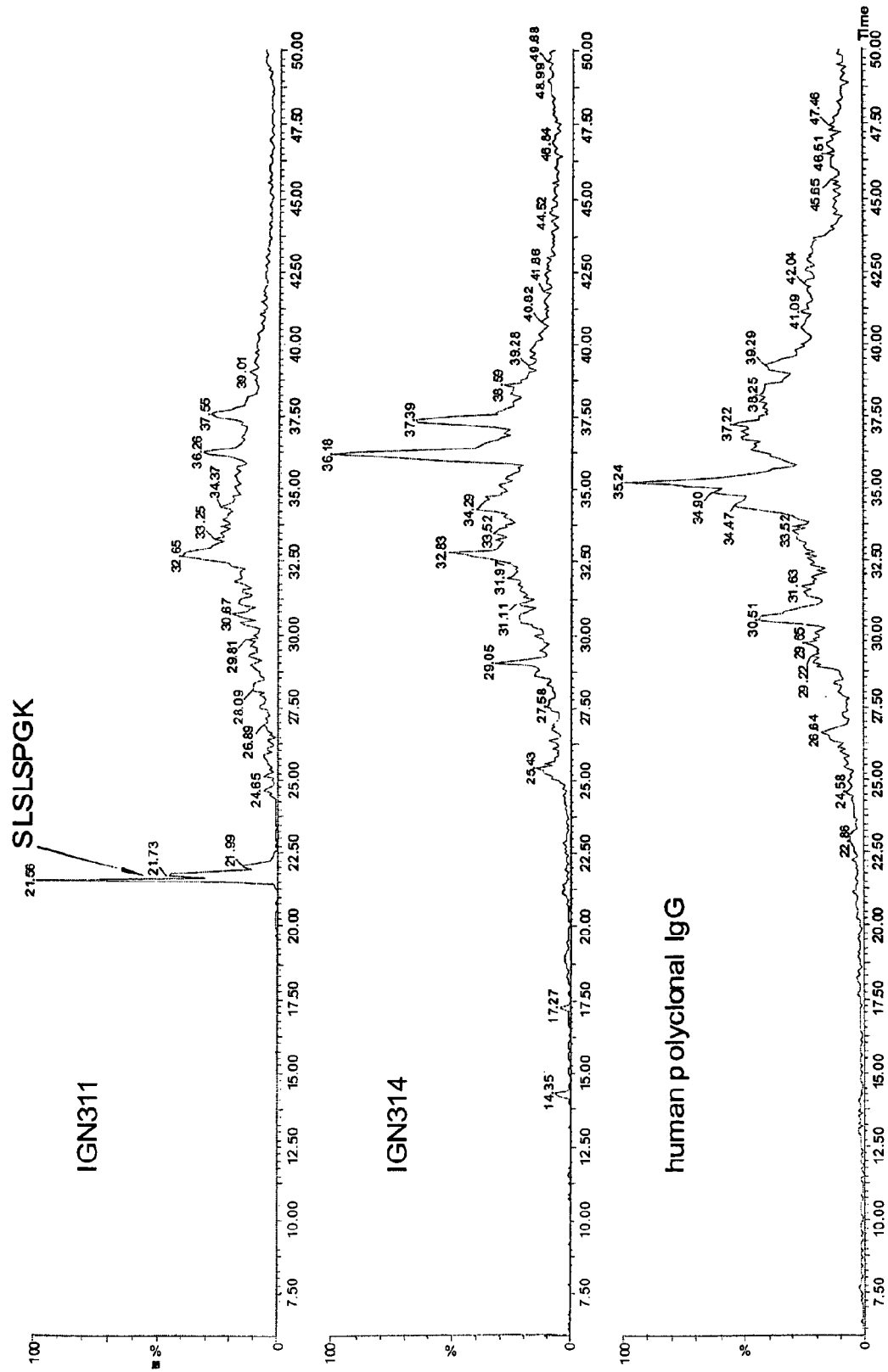

FIG. 7: (A) C18-Chromatograph of C-terminal antibody peptide SLSLSPG (SEQ ID NO: 6) of IGN311, IGN314, and human polyclonal IgG. (B) C18-Chromatograph of C-terminal antibody peptide SLSLSPGK (SEQ ID NO: 7) of IGN311; SLSLSPGK was not detected in sample IGN314 and human polyclonal IgG.

DETAILED DESCRIPTION OF THE INVENTION

Terms as used herein as generally used in the art, unless otherwise defined as follows.

The term antibody includes antibodies or antibody derivatives or fragments thereof and the specifications of the antibodies also apply to the antibody preparation of the present invention. Among the antibody fragments functional equivalents or homologues of antibodies including any polypeptide comprising an immunoglobulin binding domain or peptides mimicking this binding domain together with a Fc region or a region homologous to a Fc region or at least part of it. Chimeric molecules comprising an immunoglobulin binding domain, or equivalents, fused to another polypeptide are included.

Exemplary antibody molecules are intact immunoglobulin molecules and those portions of an immunoglobulin molecule that contains the paratope, including those portions known as Fab, Fab', F(ab')$_2$, Fc and F(v), as well as the N-glycan structure.

Surprisingly, it has been found that in one embodiment of invention the antibody according to the invention can have improved pharmacokinetics. The lack of terminal galactose residues on the antibody molecule can reduce the undesirable uptake of said antibody molecules by cells of the reticular endothelial system (like Kupffer cells in the liver) and also the uptake via asialoglycoreceptors in liver cells. This can result in less unwanted side effects and improved pharmacokinetics as well as increased half life of the antibody, resulting in prolonged efficient concentration and longer effector function of the circulating antibody towards antigen (e.g. Lewis Y, CD20, Ep-CAM, HER-2, Erb1 receptor, Erb2 receptor) expressing target cells.

As used herein, the antibody according to the invention can be expressed in host cells which cover any kind of cellular system which can be modified to express the antibody. Within the scope of the invention, the term "cells" means the cultivation of individual cells, tissues, organs, insect cells, avian cells, reptilian cells, mammalian cells, hybridoma cells, primary cells, continuous cell lines, stem cells and/or genetically engineered cells, such as recombinant cells expressing a glycosylated antibody according to the invention.

The cell systems used for recombinant expression of the antibody according to the invention can be any cell, tissue, organism from animal kingdom, for example transgenic goats, CHO cells, insect cells, human cell lines.

Preferably the cells are animal cells, for example BSC-1 cells, LLC-MK cells, CV-1 cells, CHO cells, COS cells, murine cells, human cells, HeLa cells, 293 cells, VERO cells, MDBK cells, MDCK cells, MDOK cells, CRFK cells, RAF cells, TCMK cells, LLC-PK cells, PK15 cells, WI-38 cells, MRC-5 cells, T-FLY cells, BHK cells, SP2/0, NS0 cells or derivatives thereof.

Alternatively, the cell, tissue, organism can also be from fungal kingdom or plant kingdom like yeast, tobacco, rice, alfalfa or corn. Alternatively bryophyte cells can be selected, for example from species of the genera *Physcomitrella, Funaria, Sphagnum, Ceratodon, Marchantia* and *Sphaerocarpos*. Exemplary, the bryophyte cell is *Physcomitrella patens* as used in WO 04/057002.

Alternatively an expression system can be used which has a dysfunctional or no core fucosyltransferase and/or a dysfunctional or no xylosyltransferase, and/or a dysfunctional or no 1,4-galactosyltransferase.

The galactose, fucose and/or xylose can alternatively be removed from the antibody according to the present invention by treatment with enzymes removing the residues. Any enzyme resulting in the release of galactose, fucose and/or xylose residues from N-glycans which are known in the art can be used, for example alpha-galactosidase, beta-xylosidase, alpha-fucosidase.

Alternatively an expression system can be used which synthesizes modified N-glycans which can not be used as substrates by 1,3 fucosyltransferase and/or 1,2 xylosyltransferase, and/or 1,4 galactosyltransferase.

Alternatively an expression system can be used which coexpresses basic carboxypeptidases responsible for the cleavage of C-terminal lysine residues resulting in improved cleavage rate.

Alternatively an expression system is used which comprises basic carboxypeptidases targeted for optimal localization to achieve improved cleavage of C-terminal lysine residues.

Removal of the C-terminal lysine residue can be achieved alternatively by using vector constructs lacking the codon for the C-terminal lysine on the nucleic acids encoding the heavy chain.

Alternatively the C-terminal lysine residue can be removed by in vitro processing using enzymes possessing the desired basic carboxypeptidase activity.

According to the present invention cleavage of C-terminal lysine residues can be improved by optimizing the conditions for cultivation of the cell, tissue or organism in respect to the desired cleavage of C-terminal.

The term antibody-dependent cellular cytotoxicity (ADCC) used herein refers to any activity to injury a tumor cell or the like by activating an effector cell via the binding of the Fc region of an antibody to an Fc receptor existing on the surface of an effector cell such as a killer cell, a natural killer cell, an activated macrophage or the like.

An antibody having increased ADCC activity can be determined by any suitable method known by the skilled person. One accepted assay is described in the examples.

Increased ADCC can be measured by an increased lytic potential measured as a decreased EC50 antibody concentration which indicates the antibody concentration necessary to specifically lyse the half-maximal amount of target cells.

The term complement dependent cytotoxicity (CDC) is defined as direct cell toxicity by binding and activation of complement. An antibody is binding to its target on the cell surface of e.g. the tumor cell and initiates the complement system, also known as "complement cascade" resulting in a membrane attack complex that literally makes a hole within the cell membrane, causing cell lysis and death.

An antibody having decreased CDC activity can be determined by any suitable method known by the skilled person. One accepted assay is described in the examples.

Decreased CDC activity can be defined as an increased EC50 antibody concentration which enables the lysis of the half-maximal amount of target cells. The CDC activity of the antibody according to the present invention can be up to 10% decreased, alternatively up to 20%, alternatively up to 30%. In other embodiments the CDC activity is unmodified.

The binding activity of the inventive antibody to the target antigen, e.g. Lewis Y antigen, CD20, Ep-CAM or Her-2, is at least 80% compared to the parental antibody, preferentially at least 90%, more preferentially at least 100% as compared to the parental antibody.

A possible treatment objective is the effective binding and reduction of tumor cells, i.e. tumor tissue or metastases or, in particular, disseminated tumor cells. The number of tumor cells, or micrometastases, respectively, detectable in blood, bone marrow or organs shall be significantly reduced. The formation of metastases is to be retarded, their growth is at least to be slowed down. Thus, the relapse-free life span and thus also the total survival time of the patients can be lengthened by the specifically targeted immunotherapy.

Within the scope of the use according to the invention, in particular the treatment for reducing, or inhibiting, respectively, the growth of tumor cells in a cancer patient, also a hemodialysis is possible.

According to the invention, a pharmaceutical preparation containing the antibody according to the invention in a pharmaceutical carrier or diluent is covered. The preparation can be used for preparing a medicament for the prophylactic and/or therapeutic treatment for the reduction or inhibition, respectively, of the growth of tumor cells in a patient. Reduction of tumor cell growth can be at least 5% increased compared to the use of the unmodified antibody specific for the same antigen.

A preparation containing the antibody according to the present invention is also useful for the manufacture of a medicament for the treatment of solid cancer, preferably of epithelial origin or minimal residual disease.

The inventive antibody can be used for passive immunotherapy.

Also provided is the use of the inventive antibodies or their preparation for a screening method (preferably in vitro) comprising providing a sample of a subject, preferably a human, and detecting binding events of the antibodies to an antigen in the sample. Similarly, the screening method is provided comprising providing a sample of a subject (e.g. a human), contacting the sample with the antibodies and detecting binding events. With this method subjects can be identified which can be treated with the inventive antibodies. Also the optimal antibody/preparation can be identified for a treatment of a particular disease or subject. Also provided is the method of diagnosing a specific disease comprising providing a sample of a subject (which may suffer from the disease) contracting the sample with inventive antibodies specific for an antigen which is characteristic of the disease, detecting binding events of the antibodies with antigens in the sample and diagnosing the disease if binding events are detected.

For binding all the specified receptors (antigens of the modified antibody/preparation) of a tumor cell, usually doses of at least 1 mg/dose, preferably at least 10 mg/dose, most preferred at least 50 mg/dose per patient are administered. The maximum dose will depend on the tolerability of the antibody, humanized antibodies, and human antibodies, respectively, being best tolerated. A dose of up to 1 g or in some instances up to 2 g per patient and treatment may very well be advantageous.

Surprisingly, it has been shown in the present invention that due to the increased ADCC activity the amount of antibody as applied for therapeutic and/or prophylactic purpose can be reduced, yet still leading to positive therapeutic effects even in reduced doses. Due to the increased ADCC effector function the amount of antibody applied can be reduced at least 10%, preferably at least 20%, more preferably at least 30%, even more preferred at least 40%, most preferred at least 50% compared to the dosage regimen for the parental antibody.

The treatment preferably is repeated at certain time intervals, according to the half life of the antibody used, which usually is in the range of from 3 to 30 days. By particularly derivatizing the antibody it is possible to increase the half life to up to several months and to thereby lengthen the treatment intervals accordingly.

The medicament used according to the invention preferably is provided in a suitable formulation. Preferred are such formulations with a pharmaceutically acceptable carrier. The latter comprises, e.g., auxiliary agents, buffers, salts and preservatives. Preferably, a ready to use infusion solution is provided. Since an antibody is relatively stable, medicaments based on antibodies or their derivatives have the substantial advantage that they can be put on the market as a storage-stable solution, or as a formulation in a ready-to-use form. The former preferably is storage-stable in the formulation at refrigerator temperatures up to room temperature. The medicament used according to the invention may, however, also be provided in frozen or lyophilized form which may be thawed or reconstituted when required.

The concentration of the active substance of the medicament will depend on its tolerability. A particularly well tolerable preparation based on a humanized antibody can be administered directly to the patient at a high concentration without further dilution. By the preferred concentration in the range of from 0.1% to 10%, preferably from 1% to 5%, it is possible to keep low the administered volume and the corresponding time of infusion.

Usually, the medicament will be administered i.v. Likewise, however, also another parenteral or mucosal mode of administration can be chosen, which brings the active substance to a systemic or local application at the site of the tumor or of the metastases.

EXAMPLES

The following examples shall explain the present invention in more detail, without, however, restricting it.

Example 1

Material and Methods

Mammalian cell lines and moss production strains Tumor cell lines TF-1 (Kitamura, T. et al., J Cell Physiol 140, 323-334 (1989)), Ovcar-3 (Hamilton, T. C. et al., Cancer Res 43, 5379-5389 (1983)), SK-BR-3 (Trempe, G. L., Recent Results Cancer Res 57, 33-41 (1976)) were purchased from American Type Culture Collection (Manassas, Calif.). Target antigen density (Lewis Y) was measured by FACS analysis using the humanized, Lewis Y specific antibody IGN311 in a serial dilution from 1 ng/ml to 100 µg/ml. Mean fluorescence intensity (MFI) values measured at 10 µg/ml were reported for further analysis.

*Physcomitrella patens* (Hedw.) B.S.G. Δxyl-t/Δfuc-t double knockout line was used according to Koprivova, A. et al. (Plant Biotechnol J 2, 517-523 (2004). For the generation of moss protoplasts a selected Δxyl-t/Δfuc-t double knockout line was cultivated in photobioreactors as described previously (Hohe, A. & Reski, R., Plant Sci 163, 69-74 (2002)).
Production of Recombinant Antibodies Clinical grade IGN311 control antibody was expressed in SP 2.0 cells using a FCS containing hollow fiber production process and a classical down stream process including a protein A capture step.

The Δxyl-t/Δfuc-t double knockout moss-expressed, glyco-engineered IGN311 variant was called IGN314. The coding regions of IGN311 heavy and light chains—exclusive of their respective signal peptides—were PCR-amplified (pfu polymerase) and blunt-cloned into the moss expression vector p127, designed to secrete corresponding gene products by the use of a plant signal peptide (Gorr, G. & Jost, W., Bioprocessing J 4, 26-30 (2005); Weise et al. Appl Microbiol Biotechnol 70, 337-345). The resulting constructs (p127-IGN-HC and p127-IGN-LC, respectively) were verified by restriction digest and sequencing. Transformation of moss protoplasts was performed as described previously in Jost et al. Curr Genet 47, 111-120 (2005) by simultaneous use of 45 µg of each of the two constructs and with the following modifications: threefold the number of protoplasts and six fold the amount of PEG-solution (added to the protoplast/DNA mixture, followed by a 12 minutes incubation) was used along with the standard medium (3M; 480 mOsm; Jost, W. et al. Curr Genet 47, 111-120 (2005)). Since IgG titers in the standard medium turned out to be relatively low, for mass production in total 167 transformations at eight different days were performed under optimized medium conditions (1:1 mixture of standard medium with W5 medium, Baur, A. et al., J Biotechnol 119, 332-342 (2005). All media were supplemented with 0.01% (w/v) BSA. After the transformation procedure cells were kept in 400 µl medium and subsequently, 300 µl of the culture supernatant was replaced weekly by fresh, otherwise identical medium. Mock-transformations served as (non- and co-purified) negative controls. For every week supernatants of all transformations performed at one day were pooled and purified by directly loading on equilibrated 1 ml HiTrap protein A columns (Amersham). Crude culture supernatants as well as purified antibodies were analyzed by an anti-idiotypic sandwich ELISA and silver-stained SDS-PAGE.

For the generation of stably transformed plants the PEG-mediated direct DNA-transfer was performed as described previously (Jost et al. Curr Genet 47, 111-120 (2005)). The DNA was prepared by digestion of p127-IGN-HC and p127-IGN-LC with the restriction enzymes Xho I, Hind III and Sca I. The DNA bands related to the Xho I/HindIII digestion—comprising expression promoting sequences, the coding sequences for the light or heavy chain fused to the plant signal peptide and the termination signal—were separated by gel-electrophoresis, excised and eluted from the gel-matrix. Protoplasts were isolated from Δxyl-t/Δfuc-t double knockout lines and co-transformed with 5 µg of each of the linearized and eluted DNA constructs. Following the transformation procedure and subsequent dilution and washing steps protoplasts were incubated in regeneration medium (Knop medium containing 6% glucose and 3.6% mannit, pH 5.6, ~580 mOsm) over night at 5 µmol m-2s-1 followed by light incubation at 40-50 µmol m-2s-1 for 7-10 days.

Transgenic lines containing both constructs and producing assembled IGN 314 were isolated by screening for antibody production with an anti-idiotypic sandwich ELISA. Identified transgenic lines were further cultivated in Knop medium.
Determination of N-Linked Oligosaccharide Profiles Heavy chains of samples IGN311 and IGN314 were isolated by reducing SDS-PAGE as described in Kolarich, D. & Altmann, Anal Biochem 285, 64-75 (2000). Coomassie-stained bands were excised, destained, carbamidomethylated, digested with trypsin and extracted from gel pieces as described by Kolarich, D., supra. Extracts were taken to dryness in a Speed Vac concentrator and reconstituted with water containing 0.1% formic acid. Mass spectrometric analysis was performed on a Q-TOF Ultima Global (Waters Micromass) equipped with a standard electrospray unit, a Cap-LC system (Waters Micromass) and a 10-port solvent switch module (Rheodyne). Samples were at first captured by an Aquasil C18 precolumn (30×0.32 mm, Thermo Electron) using water as the solvent. The analytical column was held at 5% acetonitrile before solvent switching and then a linear gradient from 5 to 50% acetonitrile was applied at a flow rate of 2 µl/min. All eluents contained 0.1% formic acid. Mass tuning of the TOF analyzer was done in the tandem MS mode using again [Glu1]-fibrinopeptide B. Samples were analyzed in the MS mode. Because no switching between MS and tandem MS mode was performed, no loss of signal, especially for the analysis of the glycopeptides, occurred. Data analysis was performed with MassLynx 4.0 SP4 Software (Waters Micromass).
Analytical Methods Integrity, molecular weight and potential degradation products of purified expression product were analyzed by SDS-PAGE using a Novex electrophoresis system (Invitrogen) on NuPAGE 4-12% Bis-Tris gels according to the instructions of the manufacturer. Gels were silver-stained (SilverQuest; Invitrogen). Size exclusion HPLC was performed to analyze antibodies in terms of purity, integrity and potential degradation. Samples were analyzed using a ZOR- BAX G-250 (Agilent-technologies) column in a Dionex HPLC system. To disintegrate potential aggregates and to inhibit potential precipitation, 220 mM $NaH_2PO_4$ (pH=7.0) with 10% acetonitrile ($CH_3CN$) was used as running buffer (flow 1 ml/min). Effluent was monitored online at 214 nm and 280 nm. Product concentration was calculated by standardization on a polyclonal human IgG (Pentaglobin®, Biotest) by peak integration.

Endotoxin concentration was determined using a commercially available LAL detection kit (Charles River Laboratories) according to the manufactures instructions.

Flow cytometry data were collected on a FACS-CALIBUR instrument (Becton Dickinson). Antigen expression on investigated cell lines was quantified using the human Lewis-Y specific antibody IGN311 in a concentration range from 100 µg/ml to 1.6 ng/ml. Evaluation was performed at 10 mg/ml.

Determination of Binding Specificity

Binding activity of the expression products was analyzed in a specific sandwich ELISA by incubating antibody samples in serial dilutions (from 100 µg to 1 µg/ml) in microtiter wells coated with the monoclonal anti-idiotypic antibody MMA383 (Perkins, M. et al., Pharm Res 17, 1110-1117 (2000)). After blocking with 5% FCS and washing, bound expression product was determined by reaction with a goat-immunoglobulin-peroxidase conjugate specific for human IgG, IgM and IgA (Zymed, Calif.) and stained with o-phenylenediamine/hydrogen peroxide. Optical densities (492 nm) were plotted versus logarithm of the antibody concentration (ng/ml) and fitted using a sigmoidal four parameter fit using GraphPad Prism 4 software. EC50 values were calculated and used for quantification.

Determination of Complement Dependent Cytotoxicity (CDC)

Complement mediated cell lysis activity was tested in triplicates in a $^{51}Cr$-release assay using the Lewis Y-positive SK-BR-3 breast cancer cell line as target. Target cells were incubated for one hour with 100 µCi of $^{51}Cr$, washed twice with medium and plated at a density of 20×103 cells per well into a 96-well microplate together with a serial dilution of the sample to be analyzed (72 ng to 75 µg/ml) and complement-active serum from a volunteer donor. The plate was incubated for 1 hour at 37° C. in a $CO_2$-incubator. Supernatants were collected and counted for released $^{51}Cr$ ("Cs"). Values for spontaneous release ("Sr") and maximum release ("Mr") were measured after incubation of representative samples with medium alone and with detergent (SDS), respectively. Complement mediated cytotoxicity was calculated as the percentage of cell lysis by the formula 100×(Cs−Sr)/(Mr−Sr) and was plotted against the logarithm of antibody concentration (ng/ml) and fitted using a sigmoidal four parameter fit using GraphPad Prism 4 software. EC50 values were calculated and used for quantification. Samples with negative lysis data were set to 0%.

Determination of Antibody Dependent Cellular Cytotoxicity (ADCC)

ADCC was tested in triplicates in a $^{51}Cr$ release assay using various Lewis Y-positive cancer cell lines as target cells (SK-BR-3, TF-1, Kato-III and Ovcar 3). Target cells were incubated for one hour with 100 µCi of $^{51}Cr$, washed, and plated at a density of 25×103 cells per well into 96-well microplates. Effect- or cells (PBMCs from a healthy volunteer donor) were freshly prepared and added to the target cells to achieve E:T ratios of 40:1 together with serial dilutions (100 µg to 10 µg/ml) of the antibody sample to be analyzed. After incubation at 37° C. for 16 hours in a $CO_2$-incubator, cell supernatants were collected and counted for released $^{51}Cr$ ("Cs"). Values for spontaneous release ("Sr") and maximum release ("Mr") were measured after incubation of representative samples with medium alone and with detergent (SDS) respectively. Cytotoxicity was calculated as percentage of cell lysis by the formula 100×(Cs−Sr)/(Mr−Sr). The percentage cytotoxicity was plotted against the logarithm of the antibody concentration (ng/ml) and fitted using a sigmoidal four parameter fit using GraphPad Prism 4 software. EC50 values were calculated and used for quantification.

CD16 Genotyping of PBMC Donors

CD16 (FcγRIIIa)-158$_{V/F}$ polymorphism was analyzed by a PCR-based allele-specific restriction analysis assay slightly modified from a method as described by Koene, H. R. et al., Blood 90, 1109-1114 (1997).

Results: Expression and Characterization of IGN314

Figure 3:
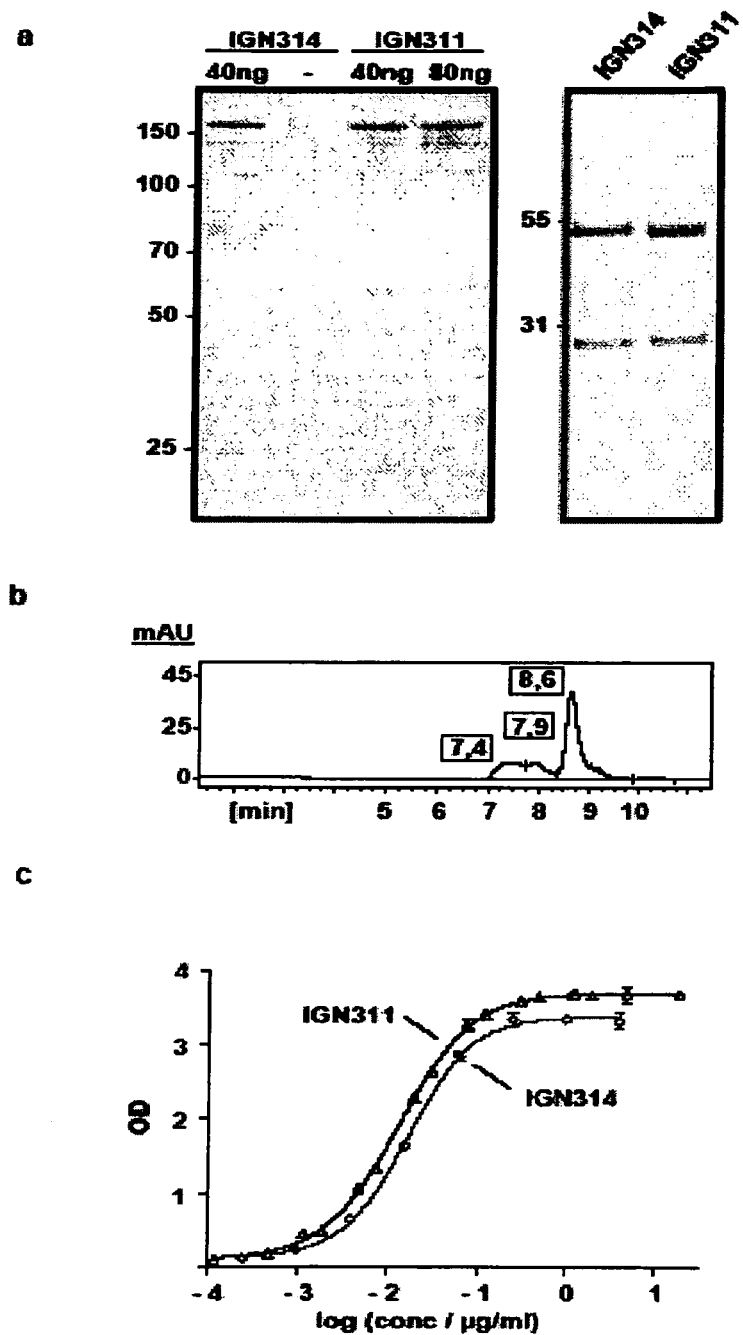
FIG. 3: Characterization of purified antibody IGN314

Moss Δxyl-t/Δfuc-t protoplasts were transiently transformed with heavy and light chain expression constructs (p127-IGN-HC, p127-IGN-LC) and IgG1 titers in pools of culture supernatants were estimated weekly by an anti-idiotypic sandwich enzyme-linked immunosorbent assay (ELISA). Under standard culture conditions IgG1 titers were found to be relatively low (0.1-0.5 µg/ml). However, IGN314 secretion significantly increased for a period of over three month under optimized media conditions. In total, this resulted in 3.8 mg IGN314 within 14 weeks for all 167 transformations performed (overall average: 6.1 µg/ml), with already 2.0 mg gained after 5 weeks of sample harvesting. Silver-stained sodium dodecyl sulfate (SDS)-polyacrylamide gels of crude culture supernatants—besides a general low background of contaminative proteins in the moss culture—revealed no supplementary bands corresponding to proteolytically processed or impaired heavy or light chains or smaller antibody fragments and proved a high rate of complete IgG1 assembly. Culture supernatants were pooled, subjected to protein-A purification and purified IGN314 was analyzed in SDS-polyacrylamide gel electrophoresis (PAGE), size exclusion high performance liquid chromatography (HPLC) as well as in an anti-idiotypic sandwich ELISA in order to test its antigen-binding specificity. Results are given in FIG. 3 and proved the integrity of IGN314 with respect to IgG1 assembly, purity and target antigen affinity. Furthermore, a peptide mapping of heavy and light chains was performed and in both cases an accurate cleavage of the plant signal-peptide as well as identical primary amino acid sequences of IGN311 and IGN314—including the removal of the C-terminal lysin in both heavy chains—were verified.

Liquid chromatography mass spectrometry (LC-MS) analysis revealed different N-glycosylation patterns for IGN311 and IGN314 heavy chains, respectively (FIG. 4). Most notably the samples differed with respect to the amount of core-fucosylation, terminal galactosylation and the degree of overall glycosylation. IGN311 was almost completely fucosylated and contained a substantial degree of terminal galactosylation, as would be expected for IgG molecules expressed in mammalian host cells. In case of IGN314 produced by the glyco-engineered moss strain used in this study no galactose- or fucose-containing glycan structure could be detected and minor amounts of IGN314 N-glycans terminated in mannose. In contrast to IGN311, IGN314 also contained a considerable amount of unglycosylated heavy chain while IGN311 was completely glycosylated. None of the two samples contained xylose residues.

Effector Functions

The lytic potential of the glyco-engineered IGN314 to the one of IGN311 was compared and it was tried to cover biological diversity aspects which may arise in cancer immunotherapy. This diversity concerns both, target and effector cells, since target antigen densities expressed on individual tumor target cells differ and patients show IgG affinity variations related to different alleles of the CD16 receptor expressed on natural killer (NK) effector cells, due to a genetic polymorphism affecting amino acid position 158 ($CD16_{158V/F}$). Hence, we analyzed on the one hand three different tumor cell lines expressing membranous Lewis Y antigen at different densities (Ovcar-3, SK-BR-3 and TF-1). These target cell lines were analyzed prior to ADCC experiments for their Lewis Y densities by fluorescence assisted cell sorting (FACS). Ovcar-3 showed the highest antigen density followed by SK-BR-3 and TF-1 (for mean fluorescence intensity values see Table 1). On the other hand, $CD16_{158}$ polymorphism of the peripheral blood mononuclear cell (PBMC) donors were analyzed in order to use defined effector cell preparations and found that about 50% (5 out of 10) expressed the high affinity $CD16_{158V/V}$ phenotype (not shown). PBMC preparations from donors of both phenotypes, i.e. $158_{V/V}$ and $158_{F/F}$, were prepared for all ADCC assays. Absence of endotoxins in all samples was confirmed prior to measurements. Simultaneously purified culture supernatants of mock-transformations were also investigated and did not show any lytic activity differing from background. Results of ADCC experiments (the calculated 50% effective concentration (EC50) values) are summarized in Table 1. EC50 values measured for IGN314 were significantly lower in comparison to the ones of IGN311 meaning that IGN314 has a 7 to 40 fold enhanced lytic potential mediated by cellular cytotoxicity in comparison to the parent antibody IGN311. Furthermore an inverse correlation between Lewis Y density on target cells and EC50 concentrations was observed for both antibodies. As compared to cell lines with low Lewis Y target antigen density (TF-1), cell lines with elevated target antigen density (Ovcar-3) required much lower antibody concentrations to induce the same lysis. EC50 values measured on cell lines with moderate antigen density (SK-BR-3), as expected, ranged between those calculated for cell lines of high and low antigen densities.

At CD16 phenotype level, effector cells prepared from high affinity receptor donors ($158_{V/V}$) showed a higher lytic activity than cells obtained from $158_{F/F}$ donors, whose affinity to IgG has been reported to be lower (Shields, R. L. et al. J Biol Chem 277, 26733-26740 (2002); Niwa, R. et al. Clin Cancer Res 10, 6248-6255 (2004)). On Ovcar-3 target cells calculated EC50 values for both antibodies in a lysis experiment using PBMCs derived from a $CD16_{158V/V}$ donor were three times lower than values obtained by an identical setup using PBMCs from a $CD16_{158F/F}$ donor. In summary, an at most 40 fold reduction of IGN314 concentration lead to the same ADCC lysis effect (EC50) when compared to IGN311 (Ovcar-3, compare Table 1) and this reduction is independent of the effector cell CD16 phenotype ($158_{V/V}$ or $158_{F/F}$).

TABLE 1

Comparison of lytic potentials of IGN311 and IGN314 on cell lines with different Lewis Y target density using effector cells (NK) of both $CD16_{158}$ phenotypes (MFI: mean fluorescence intensity; EC50: 50% effective concentration).

| Target cell line | Le Y densities (MFI) | Effector cell $CD16_{158}$ Phenotype | EC50 IGN311 (µg ml-1) | EC50 IGN314 (µg ml-1) | Enhancement |
|---|---|---|---|---|---|
| OVCAR-3 | 435 | V/V | 0.315 ± 0.2 | 0.008 ± 0.005 | 39 |
| OVCAR-3 | 435 | F/F | 0.993 ± 0.3 | 0.025 ± 0.01 | 40 |
| SK-BR-3 | 213 | V/V | 1.040 ± 0.1 | 0.144 ± 0.02 | 7 |
| TF-1 | 109 | V/V | 5.318 ± 3.2 | 0.366 ± 0.06 | 15 |

In a second set of lysis experiments using SK-BR-3 target cells the lytic potential of IGN314 to activate complement (CDC) was compared to the one of IGN311 and deglycosylated IGN311. IGN311 showed the expected lysis curve (EC50 value at 19.6±1.5 µg/ml), whereas complement-mediated lytic activity of IGN314 was dramatically reduced considering top values as well as EC50 concentrations. Deglycosylated IGN311 did not show any lytic activity at all.

Serum Effects

In natural serum high concentrations of therapeutic IgG1 antibodies are needed to compensate for inhibition of antibody-dependent cellular cytotoxity by excess endogenous immunoglobulin G. Normal serum IgG levels are blocking the binding of a therapeutic IgG1 antibody to the low affinity IgG receptor (CD16) which is present on NK cells. Together with CD64, these two Fcγ receptors are the main cellular receptors mediating ADCC. One possibility to overcome the inhibitory effect of serum IgG is the application of high amounts of the therapeutic antibody. However, this approach is cost intensive and may be associated with dose related side effects caused by enhanced cross reactivity with normal tissue, enhanced complement activation, severe first-dose side effects, the induction of an human anti-human antibody (HAHA) response or the generation of immune complexes. Another approach is the use of therapeutic antibodies which have been engineered for improved affinity for Fcγ receptors. For binding of antibodies to FcγR, the presence of oligosaccharides covalently attached to the conserved Asn297 residue in the CH2-region of the antibody heavy chain is essential (FIG. 5, Panel A) and it was suggested that the carbohydrate structures stabilize a conformation that facilitates binding. As illustrated in FIG. 5, Panel B, Asn297 is located next to the receptor binding site; however, it was shown that the carbohydrate moieties are orientated away from the interface making no specific contacts with the receptor.

Regarding the glyco-modification approach, ADCC activity of antibodies can be enhanced by changing their glycosylation from a typical complex type core fucosylated to a structure lacking this core fucosylation. Such de-fucosylated antibodies can be generated by co-transfection of genes affecting the glycosylation apparatus, by expression in production hosts lacking for specific glycosylation enzymes or by altering the expression of respective enzymes.

Previously it was shown that a glyco-engineered-variant of the Lewis-Y specific humanized antibody IGN311, lacking the core fucose residues, displays a 29-fold increased ADCC reactivity on Lewis-Y positive SK-BR-5 tumour cells as compared to the wild type antibody carrying the characteristic core fucosylated N-linked oligosaccharide pattern (WO2004/062556). The de-fucosylated IGN311, termed IGN312, was generated by genetic engineering of the glycosylation machinery of the antibody-producing host by transiently co-transfecting acetyl-glycosaminyltransferase-III genes and IGN311 heavy and light chain into human embryonic kidney-EBV nuclear antigen cells. With the present invention an up to 40-fold increase in ADCC activity by expressing the IGN311 genes for heavy and light chain in an alternative glyco-optimized plant expression system, i.e. β1,2-xylosyltransferase and α1,3-fucosyltransferase knockout moss *Physcomitrella patens* was shown. In summary, utilizing both approaches—fucosyl-deficient mammalian and plant expression systems—a significant increase in the ADCC potency of the therapeutic humanized monoclonal antibody IGN314 that allows to minimize the required therapeutic dose was demonstrated. The improved ADCC activity of the glyco-engineered antibody is at least in part due to an increased binding of the Fc Part to Fcγ-RIII receptors on the effector cells, i.e. NK cells which are major players for ADCC activity found with therapeutic antibodies.

The increased affinity mediated by the de-fucosylated IGN314 can be explained by a favorable thermodynamic behavior regarding the binding to the Fcγ-RIII receptors on the effector cells in comparison to the endogenous IgG. It was investigated whether human normal serum (NHS) affects the ability of IGN311 and de-fucosylated IGN314, respectively, to perform ADCC. First, we show that IGN311 diluted in 10% or 40% of normal human serum (NHS) showed significant lower ADCC activity than in 10% fetal calf serum (FCS) indicating that NHS significantly decreases the effector function of IGN311 (FIG. 6, grey lines). In contrast, the de-fucosylated variant was not affected by NHS (FIG. 6, black lines) and additionally had a favorable $EC_{50}$ value as compared to wild type IGN311 in both FCS as well NHS. Furthermore, the data indicate that glyco-engineering of therapeutic antibodies can compensate for endogenous IgG mediated inhibition of antibody-dependent cellular cytotoxicity in vivo.

The lysis potential was evaluated at $EC_{50}$: 0.301 µg/ml (95% CI: 0.169-0.537) and 0.052 µg/ml (95% CI: 0.028-0.094) for the parental IGN311 wild-type and the glyco-modified IGN314, respectively, in 10% FCS and 1.558 µg/ml (95% CI: 0.989-2.457) and 0.126 µg/ml (95% CI: 0.065-0.244) for parental IGN311 and glyco-modified IGN314, respectively, in 40% NHS. $EC_{50}$ values were calculated using the GraphPad Prism software.

Furthermore, a limitation of classical antibody-based therapies is the functional polymorphism of Fcγ-RIII receptors on effector cells. The FcγRIII-158$_V$ isoform, which is present at lower frequency in the human population shows high affinity to both natural and glyco-engineered antibodies whereas the predominant isoform FcγRIII-158$_F$, has only high affinity to glyco-engineered antibodies. Glyco-engineering therefore dramatically increases the number of clinical responders to passive antibody therapies based on increased lytic effector functions in human serum. These data together strongly suggest that glyco-modification of therapeutic antibodies is expected to translate in superior ADCC activity in humans.

C-Terminal Lysine

Serum derived, as well as recombinantly produced, IgG1 molecules exhibit micro-heterogeneity with respect to the occurrence of their C-terminal Lys-residues. The (partial) cleavage of the conserved C-terminal Lys-residue is a post-translational event, catalysed by the action of basic carboxypeptidases with in the cell (Lazar et al., Rapid Communications in Mass Spectrometry (18), 3, 239-244, 2004).

The analysis of human polyclonal IgG with respect to its two C-terminal tryptic peptide variants ("SLSLSPGK" and "SLSLSPG-") exhibits only the processed variant ("SLSL-SPG-") to be present in the sample. Similarly, exclusively the Lys-lacking variant was found to be present in the sample of rAb IGN314 (expressed in moss-cells). In contrast to these results, both peptide variants were detected in the sample IGN311 (FIG. 7).

The invention claimed is:

1. An antibody preparation comprising modified antibodies of an animal or derivatives or fragments thereof which are specific for an antigen, wherein the antibodies or derivatives or fragments thereof comprise an N-glycan structure free of fucose, xylose, and terminal mannose, or comprise an N-glycan structure selected from $GlcNAc_2Man_3$, $GlcNAcN_2Man_3GlcNAc$, or $GlcNAc_2Man_3GlcNAc_2$, and at least 90% of the modified antibodies, derivatives or fragments thereof lack a C-terminal lysine residue.

2. The antibody preparation of claim 1, wherein at least 95% of the modified antibodies, derivatives or fragments thereof lack a C-terminal lysine residue.

3. The antibody preparation of claim 2, wherein at least 99% of the modified antibodies, derivatives or fragments thereof lack a C-terminal lysine residue.

4. The antibody preparation of claim 3, wherein at least 100% of the modified antibodies, derivatives or fragments thereof lack a C-terminal lysine residue.

5. The antibody preparation of claim 1, wherein the N-glycan structures of the antibodies or derivatives or fragments thereof are also free of galactose.

6. The antibody preparation of claim 1, wherein the modified antibodies or derivatives or fragments thereof of the preparation have an affinity for the antigen that is the same as that of an unmodified antibody for the same antigen.

7. The antibody preparation of claim 1, wherein ADCC activity of the preparation is less inhibited by at least 10% in an at least 10% serum solution comprising unspecific antibodies of the animal as compares to ADCC activity of an unmodified antibody preparation specific for the same antigen.

8. The antibody preparation of claim 1, wherein the N-glycan structure is $GlcNAc_2Man_3$, $GlcNAc_2Man_3GlcNAc$, or $GlcNAc_2Man_3GlcNAc_2$.

9. The antibody preparation of claim 1, wherein ADCC effector function is at least 5-fold increased compared to ADCC activity of an unmodified antibody preparation specific for the same antigen.

10. The antibody preparation of claim 9, wherein ADCC effector function is at least 10-fold increased compared to ADCC activity of an unmodified antibody preparation specific for the same antigen.

11. The antibody preparation of claim 1, wherein less than 50% of the antibodies derivatives or fragments thereof lack a N-glycan structure.

12. The antibody preparation of claim 1, wherein the animal is a mammal.

13. The antibody preparation of claim 12, wherein the mammal is a human, a camel or a mouse.

14. The antibody preparation of claim 1, wherein ADCC activity of the preparation is by at least 20% less inhibited in the solution of unspecific antibodies.

15. The antibody preparation of claim 1, wherein the modified antibodies of an animal or derivatives or fragments thereof are chimeric, humanized or human.

16. The antibody preparation of claim 1, wherein CDC activity is at least 10% decreased as compared to an unmodified antibody preparation specific for the same antigen.

17. The antibody preparation of claim 1, wherein the preparation is of IgG antibodies or a fragment or derivative thereof.

18. The antibody preparation of claim 1, wherein the preparation is of monoclonal antibodies, fragments or derivatives thereof.

19. The antibody preparation of claim 1, wherein binding of the modified antibodies, derivatives or fragments thereof to $CD16_{158\,F/F}$ is by at least 10% less inhibited in an at least 10% serum solution comprising unspecific antibodies of the animal than an unmodified antibody preparation of the animal specific for the same antigen.

* * * * *

UNITED STATES PATENT AND TRADEMARK OFFICE
CERTIFICATE OF CORRECTION

PATENT NO. : 9,051,577 B2  
APPLICATION NO. : 12/373268  
DATED : June 9, 2015  
INVENTOR(S) : Manfred Schuster et al.

Page 1 of 1

It is certified that error appears in the above-identified patent and that said Letters Patent is hereby corrected as shown below:

In The Claims

Claim 1, Column 23, Line 34:

Delete "$GlcNAcN_2Man_3GlcNAc$" and replace with -- $GlcNAc_2Man_3GlcNAc$ --.

Signed and Sealed this  
Seventeenth Day of November, 2015

Michelle K. Lee  
*Director of the United States Patent and Trademark Office*

SEQUENCE LISTING

```
<160> NUMBER OF SEQ ID NOS: 7

<210> SEQ ID NO 1
<211> LENGTH: 112
<212> TYPE: PRT
<213> ORGANISM: Artificial
<220> FEATURE:
<223> OTHER INFORMATION: recombinant antibody variable region

<400> SEQUENCE: 1

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Ser Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Leu Glu Ile Lys
            100                 105                 110

<210> SEQ ID NO 2
<211> LENGTH: 119
<212> TYPE: PRT
<213> ORGANISM: Artificial
<220> FEATURE:
<223> OTHER INFORMATION: recombinant antibody variable region

<400> SEQUENCE: 2

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Asp Tyr
            20                  25                  30

Tyr Met Tyr Trp Val Arg Gln Ala Pro Glu Lys Arg Leu Glu Trp Val
        35                  40                  45

Ala Tyr Ile Ser Asn Gly Gly Ser Ser His Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr His Cys
                85                  90                  95

Ala Arg Gly Met Asp Tyr Gly Ala Trp Phe Ala Tyr Trp Gly Gln Gly
                100                 105                 110

Thr Leu Val Thr Val Ser Ser
            115

<210> SEQ ID NO 3
<211> LENGTH: 119
<212> TYPE: PRT
<213> ORGANISM: Artificial
<220> FEATURE:
<223> OTHER INFORMATION: recombinant antibody variable region

<400> SEQUENCE: 3

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Glu Lys Arg Leu Glu Trp Val
        35                  40                  45

Ala Tyr Ile Ser Asn Gly Gly Gly Ser His Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Leu Tyr His Cys
                85                  90                  95

Ala Arg Gly Met Asp Tyr Gly Ala Trp Phe Ala Tyr Trp Gly Gln Gly
                100                 105                 110

Thr Leu Val Thr Val Ser Ser
            115

<210> SEQ ID NO 4
<211> LENGTH: 13
<212> TYPE: PRT
<213> ORGANISM: Artificial
<220> FEATURE:
<223> OTHER INFORMATION: glycopeptide

<400> SEQUENCE: 4

Thr Lys Pro Arg Glu Glu Gln Tyr Asn Ser Thr Tyr Arg
1               5                   10

<210> SEQ ID NO 5
<211> LENGTH: 9
<212> TYPE: PRT
<213> ORGANISM: Artificial
<220> FEATURE:
<223> OTHER INFORMATION: glycopeptide

<400> SEQUENCE: 5

Glu Glu Gln Tyr Asn Ser Thr Tyr Arg

```
<210> SEQ ID NO 6
<211> LENGTH: 7
<212> TYPE: PRT
<213> ORGANISM: Artificial
<220> FEATURE:
<223> OTHER INFORMATION: C-terminus of recombinant antibody

<400> SEQUENCE: 6

Ser Leu Ser Leu Ser Pro Gly
1               5

<210> SEQ ID NO 7
<211> LENGTH: 8
<212> TYPE: PRT
<213> ORGANISM: Artificial
<220> FEATURE:
<223> OTHER INFORMATION: C-terminus of recombinant antibody

<400> SEQUENCE: 7

Ser Leu Ser Leu Ser Pro Gly Lys
1               5
```